United States Patent [19]

Ohsaka et al.

[11] Patent Number: 4,739,059
[45] Date of Patent: Apr. 19, 1988

[54] FLUORINE-CONTAINING AMINE AMIDES

[75] Inventors: Yohnosuke Ohsaka, Ibaraki; Yoshio Amimoto, Takatsuki; Yoshio Negishi, Settsu, all of Japan

[73] Assignee: Daikin Industries Ltd., Osaka, Japan

[21] Appl. No.: 30,490

[22] Filed: Mar. 27, 1987

Related U.S. Application Data

[63] Continuation-in-part of Ser. No. 786,681, Oct. 11, 1985, abandoned.

[30] Foreign Application Priority Data

Oct. 22, 1984 [JP] Japan .................................. 59-222467

[51] Int. Cl.$^4$ ............................................. C07D 295/18
[52] U.S. Cl. ..................................... 544/357; 544/360; 544/372; 546/189; 546/208; 548/524; 564/163; 564/167; 564/168; 564/194; 564/196; 564/197
[58] Field of Search ................. 546/208, 189; 548/524; 544/360, 357, 372; 564/194, 196, 163, 167, 168, 197

[56] References Cited

U.S. PATENT DOCUMENTS 4,326,071 4/1982 Bey et al. ........................ 564/197 X

FOREIGN PATENT DOCUMENTS 0136668 10/1985 European Pat. Off. .
2005264 4/1979 United Kingdom .

OTHER PUBLICATIONS

*Chemical Abstracts*, 58:7819f (1963).

Primary Examiner—Richard A. Schwartz
Attorney, Agent, or Firm—Birch, Stewart, Kolasch & Birch

[57] ABSTRACT

A novel amine amide of the formula:

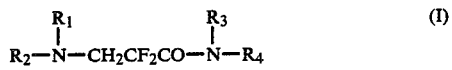

or

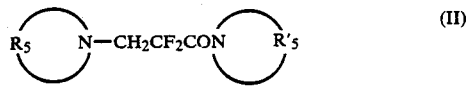

wherein the various substituents are defined hereinbelow. The compounds are useful as thickening agents, disoxidation catalysts and monomers.

1 Claim, No Drawings

FLUORINE-CONTAINING AMINE AMIDES

This application is a continuation-in-part of application Ser. No. 786,681, filed Oct. 11, 1985, now abandoned.

FIELD OF THE INVENTION

The present invention relates to novel fluorine-containing amine amide and preparation thereof.

DETAILED DESCRIPTION OF THE INVENTION

The novel amine amide according to the present invention is represented by the formula:

$$R_2-\underset{\underset{R_1}{|}}{N}-CH_2CF_2CO-\underset{\underset{R_4}{|}}{N}-R_3 \quad (I)$$

or $$R_5\text{N}-CH_2CF_2CO\text{N}R'_5 \quad (II)$$

wherein $R_1$, $R_2$, $R_3$ and $R_4$ are the same or different and each a hydrogen atom, $C_1$-$C_{18}$ alkyl group, an allyl group, a hydroxyethyl group, $$-\underset{}{\bigcirc}-R_6$$

(in which $R_6$ is a hydrogen atom, a hydroxyl group, a methoxy group, a dimethylamino group or a hydroxyethyl group), a group of the formula:

$$-R_7-\bigcirc$$

(in which $R_7$ is $-NH-$ or $-CH(COOH)CH_2-$) or a group of the formula: $-CH_2CF_2CONH-R_8$ (in which $R_8$ is a $C_1$-$C_4$ alkyl group) with the proviso that $R_2$ and $R_4$ are not hydrogen atoms; and $R_5$ and $R'_5$ are the same or different and each a $C_4$-$C_5$ alkylene which optionally contains one or two methyl groups or a group of the formula:

$$-CH_2CH_2\underset{\underset{CH_2-\bigcirc}{|}}{N}CH_2CH_2-.$$

The amine amide (I) or (II) can be prepared by reacting a monoamine of the formula:

$$HNR_1R_2, HNR_3R_4, HN\quad R_5, \text{ or } HN\quad R'_5$$

wherein $R_1$, $R_2$, $R_3$, $R_4$, $R_5$ and $R'_5$ are the same as defined above with 2,2,3,3-tetrafluorooxetane (hereinafter referred to as "tetrafluorooxetane") of the formula:

$$\begin{array}{c} CF_2-CF_2 \\ | \quad\quad | \\ CH_2-O \end{array} \quad (III)$$

in a suitable solvent. The reaction is preferably carried out in the presence of a base or a basic salt to neutralize hydrogen fluoride liberated during the reaction.

The solvent is preferably one stable against the base. Specific examples of the solvent are diethyl ether, tetrahydrofuran, methylene chloride, 1,1,2-trichlorotrifluoroethane, benzene, toluene, diethyleneglycol dimethyl ether and the like.

Specific examples of the base and the basic salt are hydroxides of alkali metals or alkaline earth metals (e.g., sodium hydroxide, potassium hydroxide, calcium hydroxide, etc.) and salts of alkali metals with weak acids (e.g., sodium carbonate, potassium carbonate, etc.).

The reaction temperature is usually from ice-cooled temperature to a reflux temperature of the solvent, preferably up to a temperature generated by a reaction heat.

The monoamine may be any one of known monoamines. Since the reaction proceeds between the amino group of the monoamine and tetrafluorooxetane, it is not affected by the kinds of the groups $R_1$, $R_2$, $R_3$ and/or $R_4$. Any amino acid can be used as the monoamine according to the present invention. The reaction according to the present invention is not influenced by the chain length of these groups.

Tetrafluorooxetane is a known compound and may be prepared by reacting tetrafluoroethylene and paraform in anhydrous hydrogen fluoride.

The fluorine-containing amine amides according to the present invention are useful as a thickening agent, a disoxidation catalyst and a monomer. In addition, some of them may be used as color display components.

The present invention will be hereinafter explained further in detail by following examples.

EXAMPLES 1 TO 6

To a mixture of a following amine (0.4 mole) and glyme (40 ml), a mixture of tetrafluorooxetane (9 ml) and glyme (20 ml) was dropwise added with stirring. After the ceasing of exothermic reaction, the reaction mixture was cooled to around a room temperature and filtered by a suction filter. After removing glyme from the filtrate, the residue was washed with water and dried to obtain a following amine amide.

(Example 1)

$$\bigcirc-NH_2 \longrightarrow \bigcirc-NHCH_2CF_2CONH-\bigcirc$$

Yield 100%.

IR (KBr): 1,680 cm$^{-1}$ (C=O), 3,420 and 3,340 cm$^{-1}$ (N—H).

$^{19}$F-NMR: 31.7 ppm (td, 14.3 Hz).

$^{1}$H-NMR: δ=3.89 (2H, t, 13 Hz), 3.9 (1H, br, s), 6.65–6.85 and 7.1–7.6 (10H, m) and 8.1 (1H, br, s).

(Example 2)

$$\bigcirc-NHCH_3 \longrightarrow \bigcirc-\underset{\underset{CH_3}{|}}{N}CH_2CF_2CO\underset{\underset{CH_3}{|}}{N}-\bigcirc$$

Yield 36%.
IR (KBr): 1,660 cm$^{-1}$ (C=O).

(Example 3)

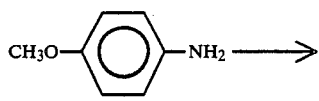

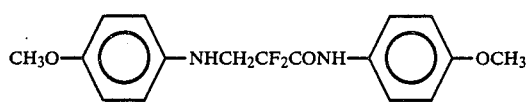

Yield 84%.
IR (KBr): 1,670 cm$^{-1}$ (C=O), 3,380 and 3,330 cm$^{-1}$ (N—H).

(Example 4)

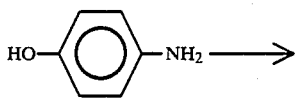

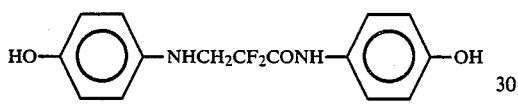

Yield 90%.
IR (KBr): 1,680 cm$^{-1}$ (C=O), 3,370 and 3,300 cm$^{-1}$ (N—H, O—H).

(Example 5)

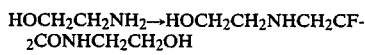

Yield 42%.
IR (neat): 1,680 cm$^{-1}$ (C=O) and 3,300 cm$^{-1}$ (N—H, O—H)

(Example 6)

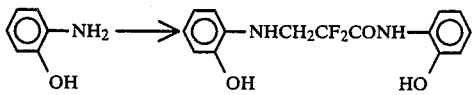

Yield 100%.
IR (neat): 1,680 cm$^{-1}$ (C=O), 3,300 cm$^{-1}$ (N—H, O—H).

EXAMPLES 7, 8 AND 9

To a mixture of a following amine (0.1 mole), an aqueous potassium hydroxide solution (5.7 g/50 ml) and diethyl ether (50 ml), a mixture of tetrafluorooxetane (4.5 ml, 0.05 mole) and diethyl ether (25 ml) was dropwise added with stirring. After the completion of the addition, the reaction mixture was stirred for another 2 hours. Then, the ether layer was separated and dried. By evaporating the ether or by filtering the precipitated product following neutralization, the product was recovered, washed with water and dried to obtain a following amine amide.

(Example 7)

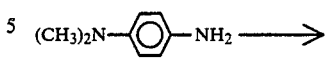

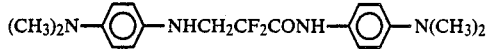

Yield 66%.
IR (KBr): 1,670 cm$^{-1}$ (C=O), 3,340, 3,320 and 3,260 cm$^{-1}$ (N—H).

(Example 8)

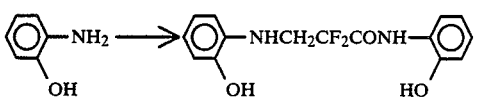

Yield 87%.

(Example 9)

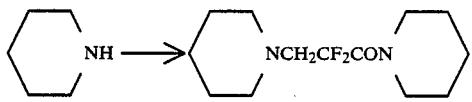

Yield 100%.
IR (neat): 1,680 cm$^{-1}$ and 1,660 cm$^{-1}$ (C=O).

EXAMPLE 10

To a solution of a following amino acid (0.1 mole) in an aqueous solution of potassium hydroxide (8.0 g/50 ml), a mixture of tetrafluorooxetane (4.5 ml) and diethyl ether (25 ml) was dropwise added. After the ceasing of the exothermic reaction, the reaction mixture was cooled to around a room temperature and filtered. To the filtrate, potassium chloride (5.56 g, 0.05 mole) was added, kept overnight and filtered. To the filtrate, concentrated hydrochloric acid (12 ml) was added to precipitate the product, which was washed with water and dried to obtain a following amine amides.

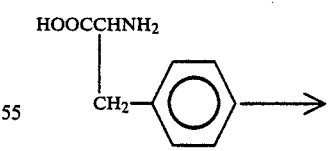

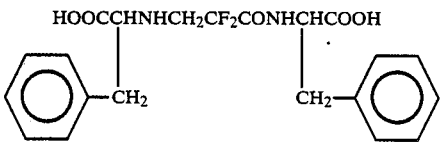

Yield 54%.
IR (KBr): 1,680 cm$^{-1}$ (C=O) and 3,330 cm$^{-1}$ (N—H).
and

HOOCCHNHCH2CF2COOH
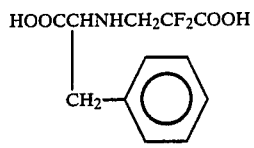

Yield 9%

IR (KBr): 1,750 and 1,640 cm$^{-1}$ (C=O) and 3,400 cm$^{-1}$ (N—H).

EXAMPLE 11

Preparation of CH3NHCH2CF2CONHCH3

To an ice-cooled mixture of a 30% aqueous solution of methylamine (50 ml, 0.44 mole) and ethyl ether (30 ml), a mixture of tetrafluorooxetane (10 ml, 0.11 mole) and ethyl ether (20 ml) was dropwise added with stirring. After 30 minutes from the completion of the addition, the mixture was refluxed for 15 minutes. The ether phase was recovered and dried over absolute sodium sulfate. From the mixture, ether was evaporated off under atmospheric pressure and then materials with lower boiling points was removed under reduced pressure of 30 mmHg at room temperature. Thereafter, the residue was simply distilled under reduced pressure of 1.5 mmHg to obtain the entitled compound (8.4 g), which solidified at room temperature. Yield 50%. Boiling point ca. 73° C./1.5 mmHg.

IR (KBr): 1,680 cm$^{-1}$ (C=O) and 3,290 cm$^{-1}$.

$^1$H-NMR (CDCl$_3$): δ(ppm)=1.34 (1H, s), 2.49 (3H, s), 2.87 and 2.92 (3H, 2s), 3.18, (2H, t, 16 Hz) and 7.2 (1H, br. s).

$^{19}$F-NMR (CDCl$_3$): 31.7 ppm (t, 14 Hz) from TFA (trifluoroacetic acid).

MS: m/e=153 (M$^+$+H), 132 (M$^+$−HF), 58.44.

EXAMPLE 12

Preparation of n—C4H9NHCH2CF2CONH—n—C4H9

A solution of potassium carbonate (15.2 g, 0.11 mole) in water (40 ml) was mixed with buthylamine (16.1 g, 0.22 mole) and ethyl ether (20 ml). To the resulting mixture, a mixture of tetrafluorooxetane (10 ml, 0.11 mole) and ethyl ether (20 ml) was dropwise added with stirring. Thereafter, the mixture was stirred for 2 hours at room temperature. The ether phase was recovered and dried over absolute sodium sulfate. From the mixture, ether was evaporated off under reduced pressure to obtain the entitled compound (23.7 g). Yield 91%. Boiling point 108°–110° C./2 mmHg.

IR (neat): 1,695 and 1,675 cm$^{-1}$ (C=O), 2,920 and 2,860 cm$^{-1}$ (C—H) and 3,280 cm$^{-1}$.

$^1$H-NMR (CDCl$_3$): δ(ppm)=0.75–0.95 (6H, m), 1.1–1.6 (9H, m), 2.60 (2H, br. t, 7 Hz), 3.11 (2H, t, 14 Hz), 3.1–3.4 (2H, m) and 7.2 (1H, br. s).

$^{19}$F-NMR: 31.7 ppm (t, 15 Hz) from TFA.

EXAMPLE 13

Preparation of n—C6H13NHCH2CF2CONH—n—C6H13

A solution of potassium carbonate (37.5 g, 0.27 mole) in water (75 ml) was mixed with hexylamine (50.6 g, 0.50 mole) and benzene (40 ml). To the resulting mixture, a mixture of tetrafluorooxetane (23 ml, 0.25 mole) and benzene (35 ml) was dropwise added with stirring. After the completion of the addition, the mixture was stirred for 2 hours at room temperature. Then, the benzene phase was recovered and the aqueous phase was extracted with benzene (30 ml×5). The benzene phase was was combined with the benzene extracts and dried over absolute sodium sulfate. From the mixture, benzene was evaporated off under reduced pressure to obtain the entitled compound (71.5 g). Yield 97%.

$^1$H-NMR (CDCl$_3$): δ(ppm)=0.8–1.0 (6H, m), 1.2–1.7 (17H, m), 2.69 (2H, br. t), 3.20 and 3.29 (4H, t and br. t) and 7.05 (1H, br. s).

$^{19}$F-NMR (CDCl$_3$): 31.6 ppm (t) from TFA.

EXAMPLE 14

Preparation of CH2=CHCH2NHCH2CF2CONHCH2CH=CH2

A solution of potassium hydroxide (1.25 g, 0.022 mole) in water (6 ml) was mixed with a solution of allylamine (3-aminopropene) (1.25 g, 0.22 mole) in 1,1,2-trichloro-1,2,2-trifluoroethane (5 ml). To the resulting mixture, a mixture of tetrafluorooxetane (1 ml, 0.11 mole) and 1,1,2-trichloro-1,2,2-trifluoroethane (1 ml) was added with ice cooling and shaken for one minute. Then, the organic phase was recovered and dried over absolute sodium sulfate. From the mixture, the solvent was evaporated off under reduced pressure to obtain the entitled compound (1.43 g). Yield 63%.

IR (neat): 1,680 cm$^{-1}$ (C=O) and 3,300 cm$^{-1}$.

EXAMPLE 15

Preparation of

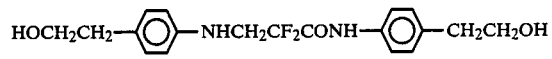

A solution of potassium carbonate (6.1 g, 0.044 mole) in water (6 ml) was mixed with a solution of p-amino-β-phenethyl alcohol (12.1 g, 0.088 mole) in glyme (150 ml). To the resulting mixture, a mixture of tetrafluorooxetane (4 ml, 0.042 mole) and glyme (16 ml) was dropwise added with stirring. After continuing stirring overnight at room temperature, glyme was distilled off under reduced pressure. To the residue, water (200 ml) was added and an undissolved compound was collected by a suction filter. After air drying, the product was recrystallized (glyme-benzene) and purified by a column (glyme/silica) to collect fractions having Rf (ethyl acetate/SiO$_2$)≠0 and minimum. From the combined fractions, glyme was distilled off under reduced pressure, and the residue was washed with benzene to obtain the entitled compound (4.4 g). Yield 29%.

IR (KBr): 1,680 cm$^{-1}$ (C=O), 3,400 and 3,330 cm$^{-1}$.

$^1$H-NMR (DIMSO-d$_6$): δ(ppm)=2.5–2.8 (4H, m), 3.4–3.65 (4H, m), 3.82 (2H, td, 14 HZ, 6 Hz), 4.48 and 4.58 (2H, 2t, 5 Hz), 5.75 (1H, t, 6 Hz), 6.63 (2H, d, 9 Hz), 6.91 (2H, d, 9 Hz), 7.16 (2H, d, 9 Hz), 7.51 (2H, d 9 Hz) and 10.25 (1H, s).

$^{19}$F-NMR: 30.7 ppm (t) from TFA.

EXAMPLE 16

Preparation of

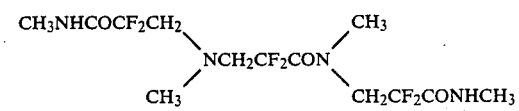

A solution of potassium carbonate (1.50 g, 10.9 mmole) in water (10 ml) was added to a solution of N,N'-dimethyl-3-amino-2,2-difluoropropionamide (1.93 g, 12.7 mmole) in ethyl ether (15 ml). To the resulting mixture, a mixture of tetrafluorooxetane (0.95 ml, 10.5 mmole) and ethyl ether (5 ml) was dropwise added with stirring. After the completion of the addition, the mixture was refluxed for 3 hours. Then, the ether phase was recovered and dried over absolute sodium sulfate. From the mixture, ether was evaporated off under reduced pressure to obtain the entitled compound (2.2 g). Yield 88%.

$^1$H-NMR (CDCl$_3$): δ(ppm)=2.56 (3H, s), 2.84 and 2.90 (9H, 2s), 3.29 (4H, t, 14 Hz), 4.06 (2H, t, 14 Hz) and 7.2 (2H, br. s).

$^{19}$F-NMR (CDCl$_3$): 30.9 ppm (2t, 14 Hz) from TFA.

MS: m/e=395 (M$^+$+H), 393 (M$^+$−H), 374 (M$^+$−HF), 286, 266, 243, 165, 145, 122, 58 and 44.

EXAMPLE 17

Preparation of

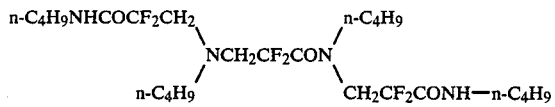

A solution of potassium carbonate (1.52 g, 11 mmole) in water (5 ml) was added to a solution of N,N'-dibuthyl-3-amino-2,2-difluoropropionamide (5.0 g, 21 mmole) in benzene (5 ml). To the resulting mixture, a mixture of tetrafluorooxetane (1.0 ml, 11 mmole) and benzene (5 ml) was dropwise added with stirring. After the completion of the addition, the mixture was refluxed for 30 minutes. Then, the benzne phase was recovered and dried over absolute sodium sulfate. From the mixture, benzene was evaporated off under reduced pressure. The residue was subjected to column chromatography and eluted by petroleum ether/ethyl ether (1:2), ethyl ether and methanol successively to collect a fraction having the minimum R$_f$ containing an entitled compound (1.35 g). Yield 23%.

$^1$H-NMR (CDCl$_3$): δ(ppm)=0.8–1.0 (12H, m), 1.1–1.7 (16H, m), 2.6–2.8 (2H, m), 2.9–3.7 (12H, m) and 7.1, 7.3 and 7.7 (2H, 3br. s).

$^{19}$F-NMR (CDCl$_3$): 29.8 ppm (2t, 14 Hz) and 31.1 ppm (t, 14 Hz) from TFA.

EXAMPLE 18

Preparation of
n—C$_{18}$H$_{37}$NHCH$_2$CF$_2$CONH—n—C$_{18}$H$_{37}$

To an ice-cooled solution of potassium hydroxide (1.2 g, 22 mmole) in water (3 ml), added were 1-aminooctadecane (5.9 g, 22 mmole) and ethyl ether (20 ml). To the resulting mixture, a mixture of tetrafluorooxetane (1.0 ml, 0.11 mmole) and ethyl ether (5 ml) was dropwise added with stirring. After the completion of the addition, the mixture was stirred for a half an hour at room temperature. Then, water was added, and the precipitate was collected by a suction filter and washed with water followed by air drying overnight to obtain the entitled compound (6.67 g). Yield 96%.

IR (KBr)=1,690 cm$^{-1}$ (C=O), 2,910 and 2,850 cm$^{-1}$ (C—H).

$^1$H-NMR (CDCl$_3$): δ(ppm)=0.89 (6H, br. t, 6 Hz), 1.27 (68H, s and m), 2.69 (2H, br. t, 6 Hz), 2.7 (1H, br. s) 3.21 (2H, t, 14 Hz), 3.30 (2H, br. t, 6H) and 7.0 (1H, br. s).

$^{19}$F-NMR (CDCl$_3$): 31.6 ppm (t, 15 Hz) from TFA.

EXAMPLE 19

Preparation of

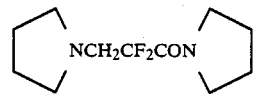

To an ice-cooled solution of potassium hydroxide (1.2 g, 22 mmole) in water (3 ml), added was a mixture of pyrrolidine (1.56 g, 22 mmole) and ethyl ether (20 ml). To the resulting mixture, a mixture of tetrafluorooxetane (1.0 ml, 0.11 mmole) and ethyl ether (5 ml) was dropwise added with stirring. After the completion of the addition, the mixture was stirred for one hour at room temperature. Then, the ether phase was recovered, washed with water and dried over absolute sodium sulfate followed by filtration. From the filtrate, ether was evaporated off under reduced pressure to obtain the entitled compound (1.91 g). Yield 75%.

IR (neat): 1,660 cm$^{-1}$ (C=O).

$^1$H-NMR (CDCl$_3$): δ(ppm)=1.7–2.0 (8H, m), 2.72 (4H, br. t, 6 Hz), 3.22 (2H, t, 16 Hz), 3.54 (2H, br. t, 6 Hz) and 3.75 (2H, br. t, 7 Hz).

$^{19}$F-NMR (CDCl$_3$): 27.6 ppm (t, 16 Hz) from TFA.

EXAMPLE 20

Preparation of

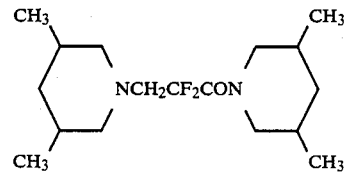

To an ice-cooled solution of potassium hydroxide (1.2 g, 22 mmole) in water (3 ml), added was a mixture of 3,5-dimethylpiperidine (2.5 g, 22 mmole) and ethyl ether (20 ml). To the resulting mixture, a mixture of tetrafluorooxetane (1.0 ml, 0.11 mmole) and ethyl ether (5 ml) was dropwise added with stirring. After the completion of the addition, the mixture was stirred for 2 hours at room temperature. Then, the ether phase was recovered, washed with water and dried over absolute sodium sulfate followed by filtration. From the filtrate, ether was evaporated off under reduced pressure to obtain the entitled compound (3.23 g). Yield 93%.

IR (neat): 1,660 cm$^{-1}$ (C=O), 2,950 and 2,900 cm$^{-1}$ (C—H).

$^1$H-NMR (CDCl$_3$): δ(ppm)=0.8–1.0 (12H, m), 1.4–2.0 (8H, m), 2.1–2.4 (2H, m), 2.5–2.7 (2H, m), 2.98 and 3.05 (2H, 2t, 16 Hz), 2.8–3.8 (2H, m) and 4.1–4.6 (2H, m).

$^{19}$F-NMR (CDCl$_3$): 22.5, 22.7, 23.0, 23.5 and 23.7 ppm (5t, 16 Hz) from TFA.

EXAMPLE 21

Preparation of

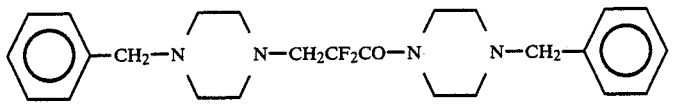

To an ice-cooled solution of potassium hydroxide (1.2 g, 22 mmole) in water (3 ml), added was a mixture of 1-benzylpiperazine (3.9 g, 22 mmole) and ethyl ether (5 ml). To the resulting mixture, a mixture of tetrafluorooxetane (1.0 ml, 0.11 mmole) and ethyl ether (5 ml) was dropwise added with stirring. After the completion of the addition, the mixture was stirred for one hour at room temperature. Then, the ether phase was recovered, washed with water (20 ml) and dried over absolute sodium sulfate followed by filtration. From the filtrate, ether was evaporated off under reduced pressure to obtain the solid entitled compound (4.78 g). Yield 98%.

IR (KBr): 1,655 cm$^{-1}$ (C=O), 2,900 and 2,800 cm$^{-1}$ (C—H).

$^1$H-NMR (CDCl$_3$): δ(ppm)=2.5 (8H, m), 2.7 (4H, m), 3.06 (2H, t, 16 Hz), 3.50 (2H, s), 3.52 (2H, s), 3.7 (4H, br. s) and 7.33 (10H, m).

$^{19}$F-NMR (CDCl$_3$): 23.4 ppm (t, 16 Hz) from TFA.

EXAMPLE 22

Preparation of

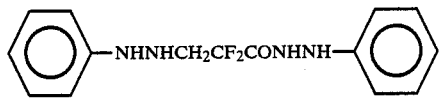

To an ice-cooled solution of potassium hydroxide (1.2 g, 22 mmole) in water (3 ml), added was a mixture of phenylhydrazine (2.4 g, 22 mmole) and ethyl ether (20 ml). To the resulting mixture, a mixture of tetrafluorooxetane (1.0 ml, 0.11 mmole) and ethyl ether (5 ml) was dropwise added with stirring. After the completion of the addition, the mixture was stirred for a half an hour at room temperature. An undissolved compound was deposited in the aqueous phase. After removing the ether phase, the deposited compound was recovered by a suction filter and washed with water followed by air drying overnight to obtain the entitled compound (1.08 g). From the ether phase, 0.68 g of the entitled compound was recovered. Total yield 52%.

IR (KBr): 1,690 cm$^{-1}$ (C=O), 3,430, 3,330 and 3,290 cm$^{-1}$ (N—H).

$^1$H-NMR (acetone-d$_6$): δ(ppm)=2.9 (1H, br. s), 3.48 (2H, t, 14 Hz), 4.5 (1H, br. s), 6.3 (1H, br. s), 6.6–7.5 (10H, m) and 9.9 (1H, br. s).

$^{19}$F-NMR (acetone-d$_6$): 33.1 ppm (t, 14 Hz) from TFA.

What is claimed is:

1. An amine amide of the formula:

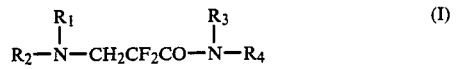

or

wherein R$_1$, R$_2$, R$_3$ and R$_4$ are the same or different and each is a hydrogen atom, C$_1$–C$_{18}$ alkyl group, an allyl group, a hydroxyethyl group,

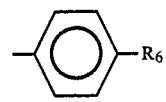

(in which R$_6$ is a hydrogen atom, a hydroxyl group, a methoxy group, a dimethylamino group or a hydroxyethyl group), a group of the formula:

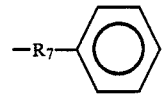

(in which R$_7$ is —NH— or —CH(COOH)CH$_2$—) or a group of the formula: —CH$_2$CF$_2$CONH—R$_8$ (in which R$_8$ is a C$_1$–C$_4$ alkyl group) with the proviso that R$_2$ and R$_4$ are not hydrogen atoms; and R$_5$ and R'$_5$ are the same or different and each is a C$_4$–C$_5$ alkylene which optionally contains one or two methyl groups or is a group of the formula:

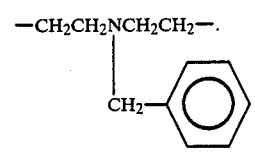

* * * * *